United States Patent [19]

Binder et al.

[11] Patent Number: 4,778,803
[45] Date of Patent: Oct. 18, 1988

[54] NITROGEN-ARYLMETHOXY-THIOPHENE DERIVATIVES AND ACID ADDITION SALTS THEREOF, AND PHARMACEUTICAL PREPARATIONS CONTAINING THESE COMPOUNDS

[75] Inventors: Dieter Binder, Vienna; Franz Rovenszky, Bruck a.d.Leitha; Hubert P. Ferber, Ansfelden, all of Austria; Karsten Schrör, Frechen-Königsdorf, Fed. Rep. of Germany

[73] Assignee: Chemie Linz Aktiengesellschaft, Linz, Austria

[21] Appl. No.: 947,418

[22] Filed: Dec. 24, 1986

[30] Foreign Application Priority Data

Jan. 17, 1986 [AT] Austria .................................. 107/86

[51] Int. Cl.⁴ ...................... A61K 31/47; C07D 215/14
[52] U.S. Cl. ...................................... 514/314; 546/152; 549/62; 549/64; 549/70; 549/71
[58] Field of Search ..................... 546/152; 549/62, 64, 549/70, 71; 514/314, 438, 445, 448

[56] References Cited

U.S. PATENT DOCUMENTS 4,292,320  9/1981  Kishimoto et al. ................. 514/307
4,329,352  5/1982  Frickel et al. ....................... 514/326
4,631,287  12/1986 Chakraborty ....................... 514/307

FOREIGN PATENT DOCUMENTS 181568  5/1986  European Pat. Off. ............ 546/152

2065121  6/1981  United Kingdom .
2068950  8/1981  United Kingdom .

OTHER PUBLICATIONS

Chemical Abstracts, vol. 88, Column 136507v (1978).

*Primary Examiner*—Donald G. Daus
*Assistant Examiner*—Mark W. Noel
*Attorney, Agent, or Firm*—Wenderoth, Lind & Ponack

[57] ABSTRACT

The invention relates to new nitrogen-arylmethoxy-thiophene derivatives of the formula I

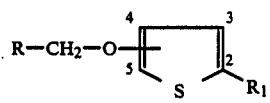

wherein the R—CH₂—O-group is in position 4 or 5 of the thiophene ring, R denotes a 2-pyridinyl- or 2-quinolinyl group and R₁ denotes a —COO-lower alkyl-, —CO—(CH₂)n—CH₃ or —CH(OH)—(CH₂)$_n$—CH₃ group, wherein n represents an integer from 2 to 6, and their hydrates and/or their pharmaceutically acceptable acid addition salts, a process for their preparation and pharmaceutical products containing these compounds. The new compounds and their salts have useful pharmacological properties. They can be used as active compounds for medicaments for the treatment and prevention of diseases, caused by a disturbance in arachidonic acid metabolism.

6 Claims, No Drawings

NITROGEN-ARYLMETHOXY-THIOPHENE DERIVATIVES AND ACID ADDITION SALTS THEREOF, AND PHARMACEUTICAL PREPARATIONS CONTAINING THESE COMPOUNDS

The invention relates to new nitrogen-arylmethoxy-thiophene derivatives of the general formula I on the sheet of formulae, in which the R—CH$_2$O— group is in position 4 or 5 of the thiophene ring, R denotes a 2-pyridinyl or 2-quinolinyl group and R$_1$ denotes a —COO-lower alkyl, —CO—(CH$_2$)$_n$—CH$_3$ or —CH(OH)—(CH$_2$)$_n$—CH$_3$ group, wherein n represents an integer from 2 to 6, and their hydrates and/or their pharmaceutically acceptable acid addition salts, a process for their preparation, pharmaceutical preparations containing these compounds and their use in medicaments.

The term "lower alkyl" designates straight-chain or branched saturated hydrocarbon radicals with 1 to 4 carbon atoms, such as methyl, ethyl, propyl, isopropyl, butyl, isobutyl or tert.-butyl.

In a preferred class of compounds of the formula I, R$_1$ denotes a —CO—(CH$_2$)$_4$—CH$_3$, —CH(OH)—(CH$_2$)$_4$—CH$_3$ or —(COO)CH$_3$ group.

The compounds 1-(5-(2-quinolinylmethoxy)-2-thienyl)-1-hexanone and -pentyl-5-(2-quinolinylmethoxy)-2-thiophenemethanol are particularly preferred.

The nitrogen-arylmethoxy-thiophene derivatives of the general formula I and acid addition salts thereof can be prepared by a process in which (a) a compound of the formula II on the sheet of formulae, in which the hydroxyl group is in position 4 or 5 of the thiophene ring and R$_2$ denotes a —COO— lower alkyl group or a —CO—(CH$_2$)$_n$—CH$_3$ group, wherein n represents an integer from 2 to 6, is reacted with a compound of the formula III on the sheet of formulae, in which R has the meaning given in the case of formula I, or with the hydrochloride thereof, in the presence of an alkali metal carbonate in a low-boiling polar organic solvent, and, if R$_2$ denotes a —CO—(CH$_2$)$_n$—CH$_3$ group, if appropriate the product is reduced with a reducing agent, to give a compound of the formula I in which R$_1$ denotes the —CH(OH)—(CH$_2$)$_n$—CH$_3$ group, or (b) if R$_1$ in formula I denotes the radical —CH(OH)—(CH$_2$)$_n$—CH$_3$ or —CO—(CH$_2$)$_n$—CH$_3$, a compound of the formula IV on the sheet of formulae, in which R has the meaning given in the case of formula I, is reacted with a compound of the formula V on the sheet of formulae, in which n denotes an integer from 2 to 6 and Y denotes the Li or MgX group, wherein X represents bromine or iodine, to give a compound of the formula I in which R$_1$ denotes the —CH(OH)—(CH$_2$)$_n$—CH$_3$ group, and, if appropriate, the compound thus obtained is oxidized with an oxidizing agent to give a compound of the formula I in which R$_1$ denotes the —CO—(CH$_2$)$_n$—CH$_3$ group, and (c) if appropriate, compounds of the formula I obtained according to (a) or (b) are converted into their pharmaceutically acceptable acid addition salts.

The alkylation of compounds of the formula II on the sheet of formulae with the halogen compounds of the formula III on the sheet of formulae by route (a) can be carried out in a polar low-boiling organic solvent, for example in acetone or butanone in the presence of at least 1 mol of anhydrous sodium carbonate or potassium carbonate. The reaction is preferably carried out in boiling 2-butanone. If the hydrochlorides of compounds of the formula III are used, a further mol of alkali metal carbonate is necessary. The reaction time is about 5-12 hours, but can also be longer or shorter than this, depending on the starting substances, the solvents and the temperature.

The reduction, carried out from case to case, of the resulting compounds of the formula I in which R$_1$ denotes a —CO—(CH$_2$)$_n$—CH$_3$ group to compounds of the formula I in which R$_1$ denotes a —CH(OH)—(CH$_2$)$_n$—CH$_3$ group can be carried out with reducing agents which are suitable for the reduction of a keto group to the alcohol group such as lithiumaluminumhydride or NaBH$_4$. It is carried out smoothly. For example, in the course of about 1 hour if NaBH$_4$ is employed in a small molar excess in an alcohol with 1-4 C atoms, preferably in ethanol, as the solvent and the mixture is heated under reflux.

The reaction of compounds of the formula IV on the sheet of formulae with the organometallic compounds of the formula V on the sheet of formulae by route (b) can be carried out under the customary conditions for Grignard reactions. It has proven appropriate here to take the organometallic compounds, dissolved in ether or tetrahydrofuran, at a temperature of −20° to +20° C. preferably at about 0° C., and to add the solution of the aldehyde of the formula IV on the sheet of formulae in an inert organic solvent, such as, for example ether or tetrahydrofuran, preferably in tetrahydrofuran, dropwise, with cooling.

The oxidation, which is carried out from case to case, of the resulting compounds of the formula I in which R$_1$ denotes a —CH(OH)—(CH$_2$)$_n$—CH$_3$ group to the ketones of the formula I can be carried out with customary oxidizing agents such as MnO$_2$ or various hexavalent chromium compounds, preferably with various hexavalent chromium compounds, for example with chromium trioxide, in glacial acetic acid or pyridine or in pyridinium chlorochromate in methylene chloride.

The compounds of the formula I have weakly basic properties. They can therefore also be converted, with corresponding strong proton acids, into crystalline pharmaceutically acceptable acid addition salts which, like, for example, the hydrochlorides, can readily be purified by recrystallization. For this, the crude base is dissolved in a suitable solvent, for example in a lower alcohol, at least the equivalent amount of a strong proton acid is added, the solvent is evaporated off in vacuo and the residue is recrystallized, for example from methanol or ethanol, if appropriate with the addition of ether. Examples of such pharmaceutically acceptable acid addition salts are, in addition to the salt of hydrochloric acid, the salt of sulfuric acid, nitric acid and phosphoric acid, and addition salts with organic acids, such as acetic acid, citric acid, oxalic acid, malonic acid, salicylic acid, methanesulfonic acid and the like. These acid addition salts have an equally potent pharmacological action as the corresponding free bases of the formula I.

The compounds of the formulae III and V are known from the literature. The compounds of the formulae II and IV can be prepared in a manner which is known per se, starting from known products.

The compounds of the formula IV can be prepared from compounds of the formula I in which R$_1$ denotes a —COO—lower alkyl group. For this, these compounds are reduced, for example with lithium aluminum hydride in tetrahydrofuran, the mixture being cooled to a temperature of less than 10° C.

The oxidation of the resulting alcohols to the desired aldehydes is preferably carried out with excess pyridinium chlorochromate in methylene chloride at room temperature.

The compounds of the formula II can be synthesized, in particular, in accordance with the following equation and the specific information in the examples.

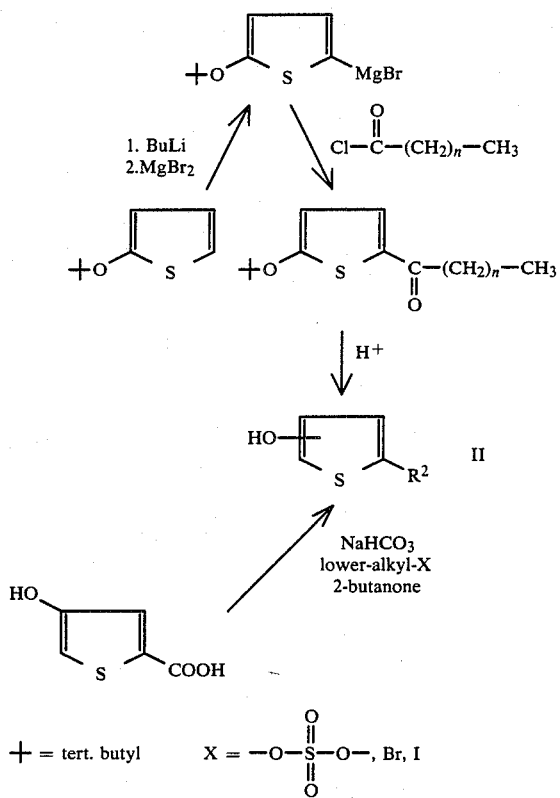

The compounds of the formula I and their pharmaceutically usable acid addition salts have useful pharmacological properties. In particular, they have a specific inhibitory action on certain enzymes, the substrate of which is arachidonic acid. These enzymes regulate biosynthesis of prostaglandins (PG), of thromboxane $A_2$ (TXA$_2$) and of the leukotrienes (LT).

Above all, 5-lipoxygenase, which converts arachidonic acid into 5-hydroperoxyeicosatetraenoic acid—a precursor of the leukotrienes—is specifically inhibited by the compounds of the formula I. In addition, the compounds of the formula I in which $R_1$ denotes the —CO—lower alkyl radical also inhibit cyclooxygenase, an enzyme which converts arachidonic acid into prostaglandin $G_2$—a precursor for other prostaglandins and TXA$_2$.

On the basis of these useful pharmacological properties, the compounds of the formula I and their pharmaceutically acceptable addition salts can be used in human medicine for diseases which are caused by a disturbance in prostaglandin, thromboxane $A_2$ or leukotriene metabolism. Such diseases are, for example, rheumatic arthritis, allergic diseases and asthma.

To investigate the pharmacological properties of the substances according to the invention, their inhibitory action on leukotriene B$_4$(LTB$_4$) formation induced by the calcium ionophor A 23-187 was measured. For this, human granulocytes were washed, the cell count was adjusted to $10^7$ cells per ml and the cells were incubated for 10 minutes at 37° C. with the compounds according to the invention, such as, for example, 1-(5-(2-quinolinylmethoxy)-2-thienyl)-1-hexanone (compound according to Example 3) or alpha-pentyl-5-(2-quinolinylmethoxy)-2-thiophenemethanol (compound according to Example 5), which had been dissolved to $10^{-2}$ M in dimethylsulfoxide and diluted to the desired concentration with physiological NaCl. The cells were then incubated for a further 10 minutes, after addition of A 23 187 (final concentration 1 μm). The reaction was stopped by addition of glacial acetic acid. The mixture was centrifuged, the supernatant was pipetted off and prostaglandin B$_2$ was added as an internal standard.

The lipid fraction was resolved via HPLC, LTB$_4$ and its 20—OH— and 20—COOH-metabolites being determined photometrically at 280 nm.

2 experiments were carried out for each concentration value of the substances according to the invention and the concentration which led to a 50% inhibition (IC$_{50}$) of LTB$_4$ formation was determined for each substance. The IC$_{50}$ here was, for example, 0.2 μM for the compound according to Example 3 and 1.0 μM for the compound according to Example 5.

The compounds of the general formula I and salts thereof can be used as medicines, for example in the form of pharmaceutical preparations which contain the compounds according to the invention mixed with a pharmaceutical organic or inorganic carrier material suitable for enteral or parenteral administration, for example water, gelatin, gum arabic, lactose, starch, magnesium stearate, talc, vegetable oils, polyalkylene glycols, vaseline or the like. The pharmaceutical preparations can be in solid form, for example as tablets, coated tablets, suppositories or capsules, or in liquid form, for example as solutions, suspensions or emulsions. If appropriate, they are sterilized and/or contain auxiliaries, such as preservatives, stabilizing agents or emulsifiers, salts for modifying the osmotic pressure or buffers. They can also be administered in combination with other therapeutically useful substances.

EXAMPLE 1

Methyl 5-(2-quinolinylmethoxy)-2-thiophenecarboxylate 8.0 g (50.6 mmol) of methyl 5-hydroxy-2-thiophenecarboxylate, 9.0 g (50.6 mmol) of 2-chloromethylquinoline and 7.0 g (50.6 mmol) of potassium carbonate are heated under reflux in 100 ml of absolute 2-butanone for 8 hours, under nitrogen. The mixture is then evaporated and the residue is partitioned between saturated sodium bicarbonate solution and methylene chloride. The aqueous phase is extracted twice more with methylene chloride and the extract is dried over sodium sulfate, with the addition of active charcoal, filtered and evaporated. The crude product (14 g of a brown oil) is dissolved in a little methanol, and excess methanolic hydrochloric acid is added. The mixture is evaporated and the residue is recrystallized from methanol.

The crystals thus obtained are partitioned between saturated sodium bicarbonate solution and methylene chloride, the aqueous phase is extracted twice more with methylene chloride and the combined organic phases are dried over sodium sulfate, filtered and evaporated. The residue is recrystallized twice from ethanol.

Yield: 3.9 g of colorless crystals (26%).
Melting point: 82°–3° C. (ethanol)

EXAMPLE 2

Methyl 5-(2-quinolinylmethoxy)-2-thiophenecarboxylate hydrochloride 1.0 g (3.34 mmol) of methyl 5-(2-quinolinylmethoxy)-2-thiophenecarboxylate is dissolved in methanol, 3.5 ml of 1N methanolic hydrochloric acid are added and the solution is evaporated to dryness. The residue is recrystallized from methanol.

Yield: 0.88 g of colorless crystals (78%).
Melting point: 136°–9° C. (methanol).

EXAMPLE 3

1-[5-(2-Quinolinylmethoxy)-2-thienyl]-1-hexanone 20.0 g (0.101 mol) of 1-(5-hydroxy-2-thienyl)-1-hexanone are heated under reflux with 13.9 g (0.101 mol) of potassium carbonate and 17.9 g (0.101 mol) of 2-chloromethylquinoline in 220 ml of absolute 2-butanone for 8 hours, under nitrogen.

The solvent is distilled off in vacuo and the residue is partitioned between ether and saturated sodium bicarbonate solution. The aqueous phase is extracted three times more with 200 ml of ether each time. The combined organic phases are washed once with water, dried over sodium sulfate/active charcoal, filtered and evaporated.

The crude product (20.0 g, 58%) is digested with diisopropyl ether and recrystallized from acetone.

Yield: 12.2 g of colorless crystals (36%).
Melting point: 86°–8° C. (acetone).

The starting material can be prepared as follows:

1-Dimethyl-ethoxy)-2-thienyl]-1-hexanone 96.0 g (0.614 mol) of 2-(1,1-dimethyl-ethoxy)thiophene are dissolved in 600 ml of absolute ether and 280 ml of a 2.5 molar solution of n-butyllithium in n-hexane (0.700 mol) are added dropwise at a temperature below 5° C. in the course of 30 minutes. The mixture is allowed to warm to room temperature and is heated under reflux for a further 2 hours.

The mixture is then cooled and magnesium bromide in ether (prepared from 117.9 g (0.738 mol) of bromine and 26.8 g (1.102 gram atoms) of magnesium in 500 ml of absolute ether) is added dropwise at a temperature below 10° C. The mixture is stirred at room temperature for a further hour.

The solution prepared above is added dropwise to a solution of 82.7 g (0.614 mol) of caproyl chloride in 250 ml of absolute ether at 17° C. in the course of 2 hours. The mixture is stirred at room temperature for a further half an hour and poured onto 1 l of saturated sodium bicarbonate solution, whereupon a dense precipitate forms. The organic phase is decanted off and the residue is washed thoroughly with ether. The combined organic phases are washed with water, dried over sodium sulfate/active charcoal, filtered and evaporated. The residue (141.8 g of a red oil, 91%) is distilled under a fine vacuum.

Yield: 59.2 g of a pale yellow oil (38%).
Boiling point: 120°–130° C./0.12–0.16 mbar.

1-(5-Hydroxy-2-thienyl)-1-hexanone 55.0 g (0.216 mol) of 1-[5-(1,1-dimethyl-ethoxy)-2-thienyl]-1-hexanone are heated under reflux in 400 ml of methanol and 24 ml of concentrated hydrochloric acid for 2.5 hours. The mixture is then evaporated in vacuo, the residue is taken up in 500 ml of ether and the mixture is washed twice with 50 ml of water each time. The organic phase is dried over sodium sulfate, filtered and evaporated. The residue (42.2 g of dark brown crystals, 99%) is digested with petroleum ether:diisopropyl ether =7:3.

Yield: 27.0 g of beige crystals (63%).
Melting point: 70°–1° C. (diisopropyl ether/petroleum ether).

EXAMPLE 4

1-5-(2-Pyridinylmethoxy)-2-thienyl]-1-hexanone 1.0 g (5.04 mmol) of 1-5-hydroxy-2-thienyl)-1-hexanone is heated under reflux with 0.75 g (4.60 mmol) of 2-chloromethylpyridine hydrochloride and 1.4 g (10.1 mmol) of potassium carbonate in 20 ml of absolute 2-butanone for 12 hours under nitrogen. The mixture is then evaporated in vacuo and the residue is partitioned between saturated sodium bicarbonate solution and ether. The product is extracted several times more with ether and the combined organic phases are dried over sodium sulfate/active charcoal, filtered and evaporated. The residue is digested with diisopropyl ether.

Yield: 0.76 g of colorless crystals (57%).
Melting point: 58°–9° C.

EXAMPLE 5

α-Pentyl-5-(2-quinolinylmethoxy)-2-thiophenemethanol 1.0 g (0.127 mol) of $NaBH_4$ is added to 7.5 g (0.022 mol) of 1-[5-(2-quinolinylmethoxy)-2-thienyl]-1-hexanone in 100 of ethanol and the mixture is heated under reflux for 40 minutes. The reaction mixture is diluted with water and extracted three times with 50 ml of methylene chloride each time. The combined organic phases are dried over sodium sulfate, filtered and evaporated. The residue is recrystallized from ethanol.

Yield: 6.5 g of colorless crystals (86%).
Melting point: 87°–90° C. (ethanol).

EXAMPLE 6

Methyl 4-(2-quinolinylmethoxy)-2-thiophenecarboxylate 4.70 g (29.7 mmol) of methyl 4-hydroxy-2-thiophenecarboxylate, 5.28 g (29.7 mmol) of 2-chloromethylquinoline and 4.11 g (29.7 mmol) of potassium carbonate are heated under reflux in 150 ml of absolute 2-butanone for 10 hours under nitrogen. The mixture is then evaporated and the residue is partitioned between saturated sodium bicarbonate solution and methylene chloride. The aqueous phase is extracted three times more with 80 ml of methylene chloride each time and the combined organic phases are dried over sodium sulfate/active charcoal, filtered and evaporated. The residue (8.87 g of reddish crystals, 100%) is recrystallized from methanol.

Yield: 4.98 g of colorless crystals (56%).
Melting point: 123°–4° C. (methanol).

The starting material can be prepared as follows:

Methyl 4-hydroxy-2-thiophenecarboxylate 50.0 g (0.347 mol) of 4-hydroxy-2-thiophenecarboxylic acid and 58.3 g (0.694 mol) of sodium bicarbonate are heated at the boiling point in 900 ml of absolute 2-butanone under nitrogen, and 43.7 g (0.347 mol) of dimethylsulfate are added dropwise in the course of 20 minutes. The mixture is heated under reflux for a further 2.5 hours. It is then evaporated in vacuo and the residue is partitioned between saturated sodium bicarbonate solution and ether. The aqueous phase is extracted five more times with 80 ml of ether each time. The combined organic phases are dried over sodium sulfate/active charcoal, filtered and evaporated.

Yield: 49.6 g of yellowish crystals (90%).

Melting point: 84°-5° C. (diisopropyl ether/petroleum ether).

EXAMPLE 7

Methyl 4-(2-quinolinylmethoxy)-2-thiophenecarboxylate hydrochloride 1.0 g (3.34 mmol) of methyl 4-(2-quinolinylmethoxy)-2-thiophenecarboxylate is dissolved in 50 ml of methanol, with gentle warming, 4 ml of 1N methanolic hydrochloric acid are added and the solution is evaporated to dryness in vacuo. The residue is recrystallized from methanol.

Yield: 1.03 g of colorless crystals (92%).

Melting point: 162°-5° C. (decomposition from 155° C., methanol).

EXAMPLE 8

Methyl 4-(2-pyridinylmethoxy)-2-thiophenecarboxylate 3.00 g (19.0 mmol) of methyl 4-hydroxy-2-thiophenecarboxylate, 3.11 g (19.0 mmol) of 2-chloromethylpyridine hydrochloride and 5.24 g (37.9 mmol) of potassium carbonate are heated under reflux in 60 ml of absolute 2-butanone for 10 hours under nitrogen. The mixture is then evaporated in vacuo and the residue is partitioned between methylene chloride and saturated sodium bicarbonate solution. The aqueous phase is extracted twice more with 100 ml of methylene chloride each time and the combined organic phases are dried over sodium sulfate/active charcoal, filtered and evaporated. The residue is digested with diisopropyl ether.

Yield: 3.12 g of colorless crystals (66%).

Melting point: 65°-6° C.

EXAMPLE 9

α-Pentyl-4-(2-quinolinylmethoxy)-2-thiophenemethanol 8.20 g (0.0543 mol) of 1-bromopentane, dissolved in 20 ml of ether, are added dropwise to 1.46 g (0.0601 gram atom) of magnesium in 50 ml of absolute ether such that a gentle reflux is maintained. When the addition has ended, the mixture is heated under reflux for a further 30 minutes. It is then cooled to −5° C. and 7.31 g (27.1 mmol) of 4-(2-quinolinylmethoxy)-2-thiophenealdehyde, dissolved in 60 ml of absolute tetrahydrofuran, is added dropwise under dry nitrogen such that the temperature does not exceed 0° C. The reaction mixture is stirred at 0° C. for a further 30 minutes and poured onto 100 ml of saturated sodium carbonate solution and 100 g of ice. The precipitate which has separated out is filtered off with suction over Hyflo, the phases are separated and the aqueous phase is extracted three times more with 100 ml of ether each time. The combined organic phases are dried over sodium sulfate/active charcoal, filtered and evaporated. The oily residue is crystallized with diisopropyl ether and recrystallized from diisopropyl ether.

Yield: 5.26 g of pale yellow crystals (57%).

Melting point: 46°-8° C (diisopropyl ether).

The starting material can be prepared as follows:

4-(2-Quinolinylmethoxy)-2-thiophenemethanol 25.0 g (83.5 mmol) of methyl 4-(2-quinolinylmethoxy)-2-thiophenecarboxylate are dissolved in 500 ml of absolute tetrahydrofuran and 2.54 g (66.8 mmol) of LiAlH$_4$ are added in portions in a countercurrent of nitrogen, with cooling, such that the temperature does not exceed 5° C. The mixture is stirred at 5° C. for a further 10 minutes and 10 ml of ice-water is then added dropwise. The hydroxide precipitate is filtered off with suction over Hyflo and washed several times with ether. The phases are separated and the aqueous phase is saturated with sodium chloride. The mixture is extracted three times more with ether and the combined organic phases are dried over sodium sulfate/active charcoal, filtered and evaporated.

Yield: 21.0 g of colorless crystals (93%).

Melting point: 126°-8° C. (methanol).

4-(2-Quinolinylmethoxy)-2-thiophenealdehyde 11.7 g (54.2 mmol) of pyridinium chlorochromate are suspended in 60 ml of absolute methylene chloride, and 9.8 g (36.1 mmol) of 4-(2-quinolinylmethoxy)-2-thiophenemethanol in 110 ml of absolute methylene chloride are added all at once at room temperature, with vigorous stirring. The mixture is stirred at room temperature for a further 1.5 hours and filtered with suction over Hyflo and the residue is washed four times with dry ether. Active charcoal is added to the filtrate, the mixture is filtered and the filtrate is evaporated. The residue is boiled up several times with a total of 400 ml of diisopropyl ether, the solution is filtered with active charcoal and concentrated to 80 ml and the concentrate is cooled to −20° C. The crystals which have precipitated are filtered off with suction and washed with a little cold diisopropyl ether.

Yield: 4.67 g of yellowish crystals (48%).

Melting point: 88°-91° C. (diisopropyl ether).

EXAMPLE 10

1-[4-(2-Quinolinylmethoxy)-2-thienyl]-1-hexanone 2.20 g (6.44 mmol) of α-pentyl-4-(2-quinolinylmethoxy)-2-thiophenemethanol are dissolved in 10 ml of glacial acetic acid and a solution of 1.40 g (14.0 mmol) of CrO$_3$ in 30 ml of glacial acetic acid is added dropwise at 20° C., with cooling. The reaction mixture is stirred for a further 30 minutes and evaporated in vacuo. 50 ml of water are added to the residue and the mixture is neutralized with potassium carbonate. It is extracted three times with 30 ml of ether each time. The combined organic phases are washed once with water, dried over sodium sulfate/active charcoal and evaporated. The oily residue (1.40 g, 64%) is crystallized with methanol and recrystallized twice from methanol.

Yield: 0.78 g of yellowish crystals (36%).

Melting point: 53°-5° C. (methanol).

What we claim is:

1. A nitrogen-arylmethoxy-thiophene of the formula:

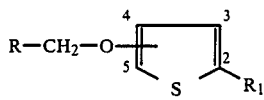

in which the R—CH₂O— group is in position 4 or 5 of the thiophene ring, R denotes a 2-quinolinyl group and R₁ denotes a —COO-lower alkyl, —CO—(CH₂)$_n$—CH₃ or —CH(OH)—(CH₂)$_n$—CH₃ group, wherein n represents an integer from 2 to 6, and/or their pharmaceutically acceptable acid addition salts.

2. The compound of claim 1, wherein R₁ denotes a —CO—(CH₂)₄-CH₃, —CH(OH)—(CH₂)₄—CH₃ or —COOCH₃ group.

3. The compound of claim 1 which is 1-(5-(2-quinolinylmethoxy)-2-thienyl)-1-hexanone.

4. The compound of claim 1 which is alpha-pentyl-5-(2-quinolinylmethoxy)-2-thiophenemethanol.

5. A pharmaceutical composition containing the compound as claimed in claim 1 in an amount effective for the treatment and prophylaxis of diseases caused by disturbances in arachidonic acid metabolism in combination with a pharmaceutically acceptable carrier or diluent.

6. A method for the treatment and prophylaxis of diseases caused by disturbances in arachidonic acid metabolism which comprises administering an effective amount of the compound of formula I as claimed in claim 1 to a patient suffering from diseases caused by disturbances in arachidonic acid metabolism.

* * * * *